United States Patent [19]
Worthington

[11] Patent Number: 5,122,529
[45] Date of Patent: Jun. 16, 1992

[54] PYRIDYL CYCLOPROPANE CARBOXAMIDINE FUNGICIDES

[75] Inventor: Paul A. Worthington, Bracknell, England

[73] Assignee: Imperial Chemical Industries plc, London, United Kingdom

[21] Appl. No.: 588,644

[22] Filed: Sep. 26, 1990

[30] Foreign Application Priority Data

Oct. 9, 1989 [GB] United Kingdom ............... 8922691

[51] Int. Cl.$^5$ .................. A61K 31/44; C07D 401/12
[52] U.S. Cl. ........................... 514/340; 514/341; 514/343; 514/318; 514/237.2; 546/275; 546/281; 546/194; 546/278; 546/279; 546/276; 540/597; 544/124
[58] Field of Search ............ 546/275, 281, 194, 278, 546/279, 276; 540/597; 544/124; 514/340, 341, 343, 318, 237.2

[56] References Cited

U.S. PATENT DOCUMENTS

| | | | |
|---|---|---|---|
| 4,281,014 | 7/1981 | Yaffe | 544/376 |
| 4,831,044 | 5/1989 | Baker et al. | 546/306 |
| 4,994,473 | 2/1991 | Broadhurst | 546/306 |

FOREIGN PATENT DOCUMENTS

| | | |
|---|---|---|
| 0015628 | 3/1980 | European Pat. Off. . |
| 0018943 | 4/1980 | European Pat. Off. . |
| 0019581 | 4/1980 | European Pat. Off. . |

*Primary Examiner*—Jane T. Fan
*Attorney, Agent, or Firm*—Michael J. Bradley

[57] ABSTRACT

A compound of general formula (II):

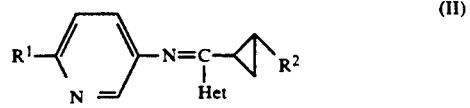

and stereoisomers thereof, wherein $R^1$ is hydrogen, halogen, $C_{1-4}$ alkoxy $C_{1-4}$ alkyl, $C_{2-4}$ alkenyl, $C_{2-4}$ alkynyl, $C_{1-4}$ haloalkyl, $C_{1-4}$ haloalkoxy, $C_{2-4}$ alkenyloxy, $C_{1-4}$ alkylcarbonyl, or cyano; $R^2$ is hydrogen, $C_{1-4}$ alkyl, $C_{1-4}$ haloalkyl or halogen; Het is a nitrogen-linked 3 to 7-membered heterocyclic ring which is optionally substituted by $C_{1-4}$ alkyl; and metal complexes and acid addition salts thereof. The compounds are useful as fungicides.

11 Claims, No Drawings

PYRIDYL CYCLOPROPANE CARBOXAMIDINE FUNGICIDES

The present invention relates to pyridyl cyclopropane carboxamidine derivatives that are useful as fungicides, to processes for preparing them, to fungicidal compositions containing them, and to methods of using them to combat fungi, especially fungal infections in plants.

Pyridyl cyclopropane carboxamidine fungicides having the formula (I):

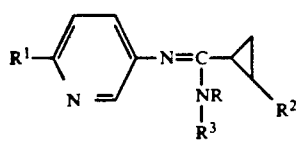

wherein R is hydrogen, pyridyl, substituted pyridyl, $C_{1-3}$ alkoxy, $C_{1-6}$ alkyl, aryl, carbamoyl, sulphonyl or cyano, and $R^3$ is hydrogen, alkyl, aryl or arylalkyl are disclosed in EP-A-0314429

According to the present invention there is provided a compound having the general formula (II):

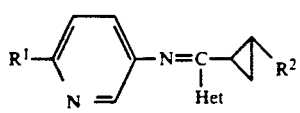

and stereoisomers thereof, wherein $R^1$ is hydrogen, halogen, $C_{1-4}$ alkoxy, $C_{1-4}$ alkyl, $C_{2-4}$ alkenyl, $C_{2-4}$ alkynyl, $C_{1-4}$ haloalkyl, $C_{1-4}$ haloalkoxy, $C_{2-4}$ alkenyloxy, $C_{1-4}$ alkylcarbonyl or cyano; $R^2$ is hydrogen, $C_{1-4}$ alkyl, $C_{1-4}$ haloalkyl or halogen; Het is a nitrogen-linked 3 to 7-membered heterocyclic ring which is optionally substituted by $C_{1-4}$ alkyl; and metal complexes and acid addition salts thereof.

Because the compounds of the invention contain an unsymmetrically substituted carbon-nitrogen double bond, they may be obtained in the form of mixtures of E and Z geometric isomers. These mixtures can, however, be separated into individual isomers by methods known in the art and such isomers and mixtures thereof in all proportions constitute a part of the present invention.

The compounds of the invention may exist as optical isomers. Such isomers and mixtures thereof in all proportions constitute a part of the present invention.

Alkyl groups and alkyl moieties of alkoxy groups contain 1 to 4 carbon atoms and are either straight or branched chain groups, for example methyl, ethyl, n-propyl, iso-propyl, n-butyl, iso-butyl, sec-butyl, or tert-butyl.

Alkenyl groups and the alkenyl moiety of alkenyloxy groups contain from 2 to 4 carbon atoms and are alk-1-enyl, alk-2-enyl or alk-3-enyl, for example vinyl, 2-prop-1-enyl, 1-prop-1-enyl, allyl, 2-but-1-enyl, 1-(2-methylprop-1-enyl), 1-but-1-enyl, 1-(2-methylprop-2-enyl), 1-but-2-enyl, 1-(1-methylprop- 2-enyl or 1-but-3-enyl.

Alkynyl groups contain from 2 to 4 carbon atoms and are, for example, ethynyl, prop-1-ynyl, propargyl, 2-but-3-ynyl, but-1-ynyl, but-2-ynyl or but-3-ynyl Haloalkyl and haloalkoxy groups contain from 1 to 4 carbon atoms and at least one halogen atom. They are either straight or branched chain and are, for example, halomethyl, haloethyl, halopropyl or halobutyl in which the halogen is fluorine, chlorine, bromine, or iodine. For example the haloalkyl groups represented by $R^1$ and $R^2$ are fluoromethyl, chloromethyl, fluoroethyl, chloroethyl, trifluoromethyl or trichloromethyl groups.

Het is a nitrogen-linked 3 to 7-membered heterocyclic ring and is optionally substituted by $C_{1-4}$ alkyl. Het can be, for example, a 3 to 7-membered saturated heterocyclic ring containing a nitrogen atom and, optionally, an oxygen or a sulphur atom. It can also be, for example, a 5- or 6-membered unsaturated heterocyclic ring containing 1, 2 or 3 nitrogen atoms and, optionally an oxygen or a sulphur atom. Het is, for example, aziridine, azetidine, pyrrolidine, piperidine, hexamethyleneimine, morpholine, imidazole, pyrazole or 1,2,4-triazole, tetrazole or pyrrole.

Halogen includes fluorine, chlorine, bromine and iodine atoms.

Metal complexes of the compounds of formula (II) include copper and zinc complexes.

Acid addition salts of the compounds of formula (II) include salts with inorganic or organic salts, for example, nitric, hydrochloric, hydrobromic, sulphuric, acetic and oxalic acids.

In one particular aspect the present invention provides a compound of general formula (II):

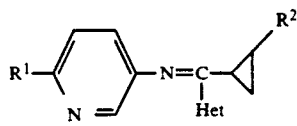

and stereoisomers thereof, wherein $R^1$ is hydrogen, halogen (especially chlorine and fluorine) or $C_{1-4}$ alkoxy (especially methoxy); $R^2$ is hydrogen, halogen (especially chlorine or fluorine) or $C_{1-4}$ alkyl (especially methyl); and Het is a nitrogen-linked 3 to 7-membered heterocyclic ring which is optionally substituted by $C_{1-4}$ alkyl.

In a further aspect the present invention provides a compound of general formula (II):

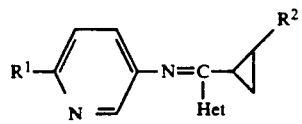

and stereoisomers thereof, wherein $R^1$ is halogen or $C_{1-4}$ alkoxy; $R^2$ is hydrogen or halogen; and Het is a nitrogen-linked 3 to 7-membered heterocyclic ring.

In another aspect the present invention provides a compound of general formula (II):

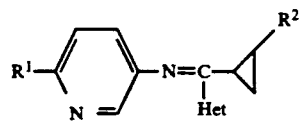

and stereoisomers thereof, wherein $R^1$ is chlorine, fluorine or methoxy; $R^2$ is hydrogen, fluorine or chlorine; and Het is a nitrogen-linked 5- or 6-membered unsaturated heterocyclic ring containing 1, 2 or 3 nitrogen atoms and, optionally an oxygen or a sulphur atom.

In a further aspect the present invention provides a compound of general formula (II):

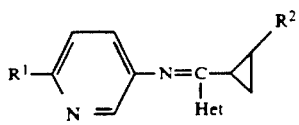

and stereoisomers thereof, wherein $R^1$ is chlorine, fluorine or methoxy; $R^2$ is hydrogen; and Het is a nitrogen-linked 5-membered unsaturated heterocyclic ring containing 1, 2 or 3 nitrogen atoms (especially pyrrole, imidazole, pyrazole and 1,2,4-triazole).

In another aspect the invention provides compounds of formula (II) in which $R^1$ is $C_{1-4}$ alkoxy (especially methoxy) or halogen (especially fluorine); $R^2$ is hydrogen; and Het is a nitrogen linked 5- or 6-membered heterocyclic ring (especially pyrazole, imidazole, 1,2,4-triazole, morpholine or piperidine).

Examples of compounds (II) according to the invention are given in Table I.

TABLE I (II)

| Compound No | $R^1$ | $R^2$ | Het | mp °C. | Comments |
|---|---|---|---|---|---|
| 1 | $CH_3O$ | H | imidazole | oil | E isomer |
| 2 | $CH_3O$ | H | 1,2,4-triazole | 62–64 | E/Z = 6:1 |
| 3 | $CH_3O$ | H | pyrazole | 66–67 | E isomer |
| 4 | F | H | imidazole | 58–60 | E isomer |
| 5 | F | H | 1,2,4-triazole | oil | E isomer |
| 6 | F | H | piperidine | oil | E isomer |
| 7 | F | H | morpholine | 94–96 | E-isomer |
| 8 | F | H | pyrazole | 41–42 | E-isomer |

TABLE I-continued (II)

R¹—[pyridine]—N=C(Het)—[cyclopropane]—R²

| Compound No | R¹ | R² | Het | mp °C. | Comments |
|---|---|---|---|---|---|
| 9 | H | H | piperidin-1-yl | oil | E-isomer |
| 10 | H | H | pyrrolidin-1-yl | oil | E-isomer |
| 11 | H | H | 2,6-dimethylmorpholin-4-yl | oil | E-isomer |
| 12 | H | H | morpholin-4-yl | oil | E-isomer |
| 13 | Cl | H | 2,6-dimethylmorpholin-4-yl | oil | E-isomer |
| 14 | F | H | 2,6-dimethylmorpholin-4-yl | oil | E-isomer |
| 15 | Cl | H | pyrrolidin-1-yl | oil | E-isomer |
| 16 | F | H | pyrrolidin-1-yl | oil | E-isomer |
| 17 | CH₃O | H | 2,6-dimethylmorpholin-4-yl | oil | E-isomer |
| 18 | CH₃O | H | pyrrolidin-1-yl | | |

TABLE I-continued $$\text{R}^1 - \underset{N}{\underset{\|}{\bigcirc}} - N = \underset{\text{Het}}{\overset{C}{|}} - \triangleleft \text{R}^2 \quad \text{(II)}$$

| Compound No | R¹ | R² | Het | mp °C. | Comments |
|---|---|---|---|---|---|
| 19 | Cl | H | 1,3-dimethylpyrazol-4-yl | oil | E-isomer |
| 20 | Cl | H | 1H-tetrazol-5-yl | | |
| 21 | CH₃O | H | 1H-tetrazol-5-yl | | |
| 22 | F | H | 1H-tetrazol-5-yl | | |
| 23 | H | H | 1H-tetrazol-5-yl | | |
| 24 | Cl | H | 2H-tetrazol-5-yl | | |
| 25 | CH₃O | H | 2H-tetrazol-5-yl | | |
| 26 | F | H | 2H-tetrazol-5-yl | | |
| 27 | H | H | 2H-tetrazol-5-yl | | |

TABLE I-continued $$\text{(II)} \quad R^1\text{-pyridine-}N=C(\text{Het})\text{-cyclopropyl-}R^2$$

| Compound No | R¹ | R² | Het | mp °C | Comments |
|---|---|---|---|---|---|
| 28 | CH₃O | H | aziridin-1-yl | | |
| 29 | Cl | H | aziridin-1-yl | | |
| 30 | F | H | aziridin-1-yl | | |
| 31 | H | H | aziridin-1-yl | | |
| 32 | Cl | H | azetidin-1-yl | | |
| 33 | F | H | azetidin-1-yl | | |
| 34 | CH₃O | H | azetidin-1-yl | | |
| 35 | H | H | azetidin-1-yl | | |
| 36 | Cl | H | 2,5-dihydro-1H-pyrrol-1-yl | | |
| 37 | F | H | 2,5-dihydro-1H-pyrrol-1-yl | | |
| 38 | CH₃O | H | 2,5-dihydro-1H-pyrrol-1-yl | | |
| 39 | H | H | 2,5-dihydro-1H-pyrrol-1-yl | | |
| 40 | Cl | H | hexahydroazepin-1-yl | | |

TABLE I-continued
(II)
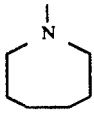
| Compound No | R¹ | R² | Het | mp °C. | Comments |
|---|---|---|---|---|---|
| 41 | F | H | 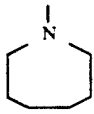 | | |
| 42 | CH₃O | H | 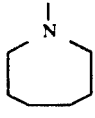 | | |
| 43 | H | H | 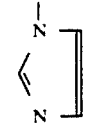 | | |
| 44 | CH₃ | H | 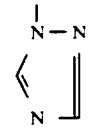 | | |
| 45 | CH₃ | H | 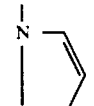 | | |
| 46 | CH₃ | H | 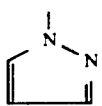 | | |
| 47 | Cl | F | 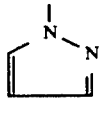 | | |
| 48 | F | F | 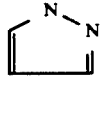 | | |
| 49 | CH₃O | F | 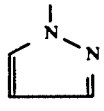 | | |
| 50 | H | F | | | |

TABLE I-continued (II)

$$R^1\text{-pyridine-}N=C(\text{Het})\text{-cyclopropyl-}R^2$$

| Compound No | R¹ | R² | Het | mp °C. | Comments |
|---|---|---|---|---|---|
| 51 | Cl | F | 1,2,4-triazol-1-yl | | |
| 52 | F | F | 1,2,4-triazol-1-yl | | |
| 53 | CH₃O | F | 1,2,4-triazol-1-yl | | |
| 54 | H | F | 1,2,4-triazol-1-yl | | |
| 55 | Cl | Cl | 1,2,4-triazol-1-yl | | |
| 56 | CH₃O | Cl | 1,2,4-triazol-1-yl | | |
| 57 | F | Cl | 1,2,4-triazol-1-yl | | |
| 58 | H | Cl | 1,2,4-triazol-1-yl | | |
| 59 | Cl | Cl | pyrazol-1-yl | | |
| 60 | CH₃O | Cl | pyrazol-1-yl | | |
| 61 | F | Cl | pyrazol-1-yl | | |

TABLE I-continued $$\text{R}^1 - \underset{N}{\underset{|}{\bigcirc}} - N = \underset{\underset{Het}{|}}{C} - \triangle - R^2 \quad (II)$$

| Compound No | R¹ | R² | Het | mp °C. | Comments |
|---|---|---|---|---|---|
| 62 | H | Cl | pyrazol-1-yl | | |
| 63 | Cl | CH₃ | pyrazol-1-yl | | |
| 64 | CH₃O | CH₃ | pyrazol-1-yl | | |
| 65 | F | CH₃ | pyrazol-1-yl | | |
| 66 | H | CH₃ | pyrazol-1-yl | | |
| 67 | Cl | CH₃ | imidazol-1-yl | | |
| 68 | F | CH₃ | imidazol-1-yl | | |
| 69 | CH₃O | CH₃ | imidazol-1-yl | | |
| 70 | H | CH₃ | imidazol-1-yl | | |

TABLE II

SELECTED PROTON NMR DATA

Table II shows selected proton NMR data for certain compounds described in Table I. Chemical shifts are measured in ppm from tetramethylsilane, and deuterochloroform was used as a solvent throughout. The following abbreviations are used:

s = singlet
d = doublet
dd = doublet of doublets
m = multiplet
t = triplet

| Compound No | |
|---|---|
| 1 | 0.60(2H,m), 1.05(2H,m), 1.95(1H,m), 3.95(3H,s) 6.75(1H,d), 7.10(1H,s), 7.30(1H,dd), 7.75 (1H,s), 7.85(1H,dd), 8.40(1H,s). |
| 5 | 1.05(2H,m), 1.30(2H,m), 2.00(1H,m), 7.00 (1H,dd), 7.45(1H,dd), 7.90(1H,d), 8.00(1H,s), 9.00(1H,s). |
| 6 | 0.40(2H,m), 1.75(2H,m), 1.45(1H,m), 1.65 (6H,m), 3.60(4H,m), 6.75(1H,dd), 7.20(1H,m), 7.65(1H,d). |
| 9 | 0.4(2H,m), 0.7(2H,m), 1.5(1H,m), 1.6(6H,m), 3.6(4H,t), 7.1(2H,m), 8.1(2H,m). |
| 10 | 0.4(2H,m), 0.75(2H,m), 1.6(1H,m), 2.0(4H,m), 3.6(4H,t), 7.15(2H,m), 8.2(2H,m). |
| 11 | 0.4(2H,m), 0.75(2H,m), 1.25(2H,d), 1.5(1H,m), 2.6(2H,dd), 3.65(2H,m), 4.3(2H,dd), 7.1(2H,m), 8.1(1H,dd), 8.15(1H,dd). |
| 12 | 0.4(2H,m), 0.75(2H,m), 1.45(1H,m), 3.7(8H,m), 7.1(2H,m), 8.1(1H,d), 8.2(1H,dd). |
| 13 | 0.4(2H,m), 0.8(2H,m), 1.05(6H,d), 1.45(1H,m), 2.6(2H,dd), 3.65(2H,m), 4.3(2H,dd), 7.05(1H,dd), 7.15(1H,d), 7.85(1H,d). |
| 14 | 0.35(2H,m), 0.75(2H,m), 1.25(6H,d), 1.45(1H,m), 2.55(2H,dd), 3.65(2H,m), 4.3(2H,dd), 6.8(1H,dd), 7.2(1H,m), 7.65(1H,d). |
| 15 | 0.4(2H,m), 0.75(2H,m), 1.55(1H,m), 1.95(4H,m), 3.55(4H,t), 7.1(2H,m), 7.9(1H,d). |
| 16 | 0.4(2H,m), 0.75(2H,m), 1.55(1H,m), 1.95(4H,m), 3.55(4H,t), 6.75(1H,dd), 7.2(1H,m), 7.7(1H,s). |
| 17 | 0.4(2H,m), 0.75(2H,m), 1.25(6H,d), 1.4(1H,m), 2.55(2H,dd), 3.65(2H,m), 3.9(3H,s), 4.25(2H,d), 6.65(1H,d), 7.1(1H,dd), 7.65(1H,d). |
| 19 | 1.05(2H,m), 1.20(2H,m), 2.00(1H,m), 2.25(6H,s), 5.90(1H,s), 7.20(2H,m), 7.90(1H,m). |

Compounds of formula (II):

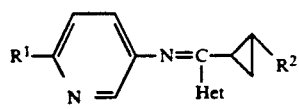
(II)

wherein $R^1$, $R^2$ and Het are as defined above, can be prepared by treating an imidoyl halide of general formula

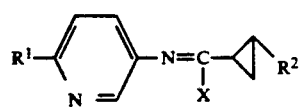
(III)

wherein $R^1$ and $R^2$ are as defined above, and X is a halogen atom, for example chlorine or bromine, with a compound of general formula (IV):

(IV)

wherein Het is as defined above, in the presence of a convenient base such as triethylamine, pyridine or dimethylaminopyridine. The reaction is carried out in an inert solvent such asmethylene chloride or diethyl ether at room temperature or at the reflux temperature of the solvent.

The imidoyl halide (III) intermediate is prepared by treating an amide of general formula (V):

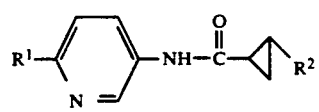
(V)

wherein $R^1$ and $R^2$ are as defined above, with an imidoylating reagent such as phosphorus pentachloride or phosphorus pentabromide, or, carbon tetrachloride or 1,2-dibromotetrachloroethane and triphenyl phosphine. The reaction is carried out in an inert solvent such as methylene chloride or 1,2-dichloroethane at a suitable temperature. Where appropriate triphenylphosphine oxide is removed by filtration. Trituration, after the addition of a suitable solvent such as n-hexane, followed by filtration may be used to remove further quantities of triphenylphosphine oxide.

Evaporation of the solvent gives the imidoyl halide (III) or the hydrochloride salt of the imidoyl halide (III).

The amide of general formula (V) is prepared by reacting a substituted pyridine of general formula (VI):

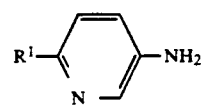
(VI)

wherein $R^1$ is as defined above, with a substituted cyclopropane carboxylic acid chloride of general formula (VII):

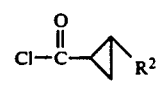
(VII)

wherein $R^2$ is as defined above, in a suitable inert solvent such as methylene chloride, chloroform, diethyl ether or tetrahydrofuran. It is usually desirable to carry out the reaction in the presence of a suitable acid scavenger such as triethylamine, pyridine, an alkaline carbonate or an alkaline hydroxide. The preparation of amides of general formula (V) is already described EP-A-0243 971.

In another aspect, the invention includes the processes above described.

The compounds of the invention are active fungicides and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca*

*fuliginea* on cucurbits (e.g. cucumber), *Podosphaera leucotricha* on apple and *Uncinula necator* on vines.

Helminthosporium spp., Rhynchosporium spp., Septoria spp., Pyrenophora spp., *Pseudocercosporella herpotrichoides* and *Gaeumannomyces graminis* on cereals.

*Cercospora arachidicola* and *Cercosporidium personata* on peanuts and other Cercospora species on other hosts, for example, sugar beet, bananas, soya beans and rice. *Botrytis cinerea* (grey mould) on tomatoes, strawberries, vegetables, vines and other hosts.

Alternaria spp. on vegetables (e.g. cucumber), oilseed rape, apples, tomatoes and other hosts.

*Venturia inaequalis* (scab) on apples.

*Plasmopara viticola* on vines.

*Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and italicum and *Trichoderma viride* on oranges, *Gloeosporium musarum* on bananas and *Botrytis cinerea* on grapes).

Further, some of the compounds may be active as seed dressings against Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (II) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (II) alone. Further the other fungicide can have a synergistic effect on the fungicidal activity of the compound of general formula (II). Examples of fungicidal compounds which may be included in the composition of the invention are (±)-2-(2,4-dichlorphenyl)-3-(1H-1,2,4-tri- azol-1-yl)propyl 1,1,2,2-tetrafluoroethyl ether, (RS)-1-aminopropylphosphonic acid, (RS)-4-(4-chlorophenyl)-2-phenyl-2-(1H-1,2,4-triazol-1-ylmethyl)butyronitrile, (RS)-4-chloro-N-(cyano(ethoxy)methyl)benzamide, (Z)-N-but-2-enyloxymethyl-2-chloro-2',6'-diethylacetanilide, 1-(2- cyano-2-methoxyiminoacetyl)-3-ethyl urea, 1-[2RS,4RS;2RS,-4RS)-4-bromo-2-(2,4-dichlorophenyl)tetrahydrofurfuryl]- 1H-1,2,4-triazole, 3-(2,4-dichlorophenyl)-2-(1H-1,2,4- triazol-1-yl)quinazolin-4(3H)-one, 3-chloro-4-[4-methyl- 2-(1H-1,2,4-triazol-1-methyl)-1,3-dioxolan)-2-yl]phenyl- 4-chlorophenyl ether, 4-bromo-2-cyano-N,N-dimethyl-6- trifluoromethylbenzimidazole-1-sulphonamide, 4-chlorobenzyl N-(2,4-dichlorophenyl)-2-(1H-1,2,4-triazol-1-yl)thioacetamidate, 5-ethyl-5,8-dihydro-oxo(1,3)-dioxolo(4,5-g)quinoline-7-carboxylic acid, α-[N-(3-chloro-2,6-xylyl)-2-methoxyacetamido]-γ-butyrolactone, anilazine, BAS 454, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, dimethamorph, dimethirimol, diniconazole, dinocap, ditalimfos, dithianon, dodemorph, dodine, edifenphos, etaconazole, ethirimol, ethyl (Z)-N-benzy-N-([methyl(methyl- thioethylideneamino-oxycarbonyl)amino]thio)-β-alaninate, etridazole, fenapanil, fenarimol, fenfuram, fenpiclonil, fenpropidin, fenpropimorph, fentin acetate, fentin hydroxide, flutolanil, flutriafol, fluzilazole, folpet, fosetyl-aluminium, fuberidazole, furalaxyl, furconazole-cis, guazatine, hexaconazole, hydroxyisoxazole, imazalil, iprobenfos, iprodione, isoprothiolane, kasugamycin, mancozeb, maneb, mepronil, metalaxyl, methfuroxam, metsulfovax, myclobutanil, neoasozin, nickel dimethyldithiocarbamate, nitrothalisopropyl, nuarimol, ofurace, organomercury compounds, oxadixyl, oxycarboxin, penconazole, pencycuron, pent-4-enyl N-furfuryl-N-imidazol-1-ylcarbonyl-DL-homoalaninate, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, thiabendazole, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin and zineb. The compounds of general formula (II) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophas, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di- methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. GA$_3$, GA$_4$ or GA$_7$) and triapenthenol.

The following Examples illustrate the invention. Reactions involving water-sensitive intermediates were performed under an atmosphere of dry nitrogen and solvents were dried before use where appropriate.

EXAMPLE 1

Preparation of N-(2-methoxy-5-pyridyl)cyclopropylmethanimidoyl pyrazole (Compound No 3 in Table I).

Stage 1

A solution of 5-amino-2-methoxy pyridine (12.4 g, 0.10 mol) and pyridine (10 ml) in dichloromethane (200 ml) was stirred at room temperature. Cyclopropane carboxylic acid chloride (9.1 ml, 0.10 mol) was added dropwise to the reaction mixture at such a rate to maintain the temperature at 20°–30° C. After complete addition the reaction mixture was stirred at room temperature for a further one hour, then washed with 5% sodium hydroxide (200 ml), water (100 ml) and dried over anhydrous magnesium sulphate. Removal of the solvent gave N-(2-methoxy-5-pyridyl)-cyclopropane carboxamide (16.7 g, 87%) m.p. 130–131° C.

Stage 2

N-(2-methoxy-5-pyridyl)-cyclopropane carboxamide (5.0 g, 0.026 mol) was added portionwise to stirred solution of phosphorus pentachloride (5.42 g, 0.026 mol) in dichloromethane (25 ml) under a nitrogen atmosphere at room temperature. After complete addition the mixture was stirred at room temperature for one hour and then heated at reflux for a further one hour. The reaction mixture was then evaporated under vacuum to give a solid product which was washed with diethyl ether (50 ml) and air dried to give N-(2-methoxy-5-pyridyl)-cyclopropylmethanimidoyl chloride as the hydrochloride salt (6.2 g, 97%) which was used in Stage 3 without further purification or characterisation.

Stage 3

Pyrazole (1.77 g, 0.026 mol) was added portionwise to a mixture of N-(2-methoxy-5-pyridyl)-cyclopropylmethanimidoyl chloride (6.2 g from the previous reaction) and triethylamine (5.26 g, 0.052 mol) in dichloromethane (25 ml) at room temperature under a nitrogen atmosphere. After complete addition the mixture was heated at reflux for four hours. The reaction mixture was then evaporated under vacuum to give a solid residue which was purified by column chromatography (silica eluted with hexane : ethyl acetate=3 : 1) to give the title compound as a white crystalline solid (2.0 g, 32%) m.p. 66–67° C.

EXAMPLE 2

Preparation of N-(2-fluoro-5-pyridyl)-cyclopropylmethanimidoyl imidazole (Compound No 4 in Table I)

Stage 1

A solution of 5-amino-2-fluoropyridine (6.63 g, 0.059 mol) and pyridine (5.16 g, 0.065 mol) in dichloromethane (120 ml) was stirred at room temperature. Cyclopropane carboxylic acid chloride (6.2 g, 0.059 mol) was added dropwise to the reaction mixture at such a rate to maintain the temperature at 20°–30° C. After complete addition the reaction mixture was stirred at temperature for a further one hour, then washed with 5% sodium hydroxide (100 ml), water (100 ml) and dried over anhydrous magnesium sulphate. Removal of the solvent gave a dark brown solid which was purified by column chromatography (silica eluted with dichloromethane : tetrahydrofuran=9:1) to give N-(2-fluoro-5-pyridyl)cyclopropane carboxamide (7.7 g, 72%) as an orange brown solid m.p. 116°–117° C.

Stage 2

N-(2-fluoro-5-pyridyl)-cyclopropane carboxamide (2.0 g, 0.011 mol) was added portionwise to a stirred solution of phosphorus pentachloride (2.31 g, 0.011 mol) in dichloromethane (20 ml) under a nitrogen atmosphere at room temperature. After complete addition the mixture was stirred at room temperature for one hour and then heated at reflux for a further one hour. The reaction mixture was then evaporated under vacuum to gave N-(2-fluoro-5-pyridyl)-cyclopropylmethanimidoyl chloride (2.1 g, 96%) which was used in Stage 3 without further purification or characterisation.

Stage 3

Imidazole (0.76 g, 0.011 mol) was added to a mixture of N-(2-fluoro-5-pyridyl)-cyclopropylmethanimidoyl chloride (2.1 g from the previous reaction) and triethylamine (2.25 g, 0.022 mol) in dichloromethane (20 ml) at room temperature under a nitrogen atmosphere. After complete addition the mixture was heated at reflux for four hours. The reaction mixture was then evaporated under vacuum to give a dark yellow oil which was purified by column chromatography (silica eluted with dichloromethane : ethyl acetate=1:1) to give the title compound (0.4 g, 20%) as a yellow solid m.p. 58°–60° C.

EXAMPLE 3

Preparation of N-(2-fluoro-5-pyridyl)cyclopropylmethanimidoyl triazole (Compound No 5 in Table I)

Stage 1

A solution of 1,2-dibromotetrachloroethane (7.23 g, 0.022 mol) in 1,2-dichloroethane (50 ml) and triethylamine (4.49 g, 0.044 mol) was added to a stirred suspension of N-(2-fluoro-5-pyridyl)-cyclopropane carboxamide (2.0 g, 0.011 mol) - see Example 2 stage 1 and triphenylphosphine (5.83 g, 0.022 mol) in 1,2-dichloroethane (25 ml) at −10° C. under nitrogen at such a rate so that the temperature did not rise above −10° C. After complete addition (1¼ hours) the reaction mixture was allowed to warm up to room temperature and any triphenyl phosphine oxide was removed by filtration. Further quantities of triphenylphosphine oxide were removed by trituration of the residue with hexane. The filtrate was evaporated to give N-(2-fluoro-5-pyridyl)-cyclopropylmethanimidoyl bromide (2.54 g, 95%) as a yellow crystalline solid which was used in the next stage without further purification or characterisation.

Stage 2

1,2,4-triazole (0.77 g, 0.011 mol) was added to a mixture of N-(2-fluoro-5-pyridyl)-cyclopropylmethanimidoyl bromide (2.54 g from the previous reaction) and triethylamine (2.25 g, 0.022 mol) in dichloromethane (20 ml) at room temperature under a nitrogen atmosphere.

After complete addition the mixture was heated at reflux for four hours, cooled to room temperature and poured into water. The organic layer was washed with brine and dried over anhydrous magnesium sulphate Removal of the solvent gave an orange oil which purified by column chromatography (silica gel eluted with diethyl ether) to give the title compound (0.53 g, 21%) as a yellow oil.

The following are examples of compositions suitable for agricultural and horticultural purposes which can be formulated from the compounds of the invention. Such compositions form another aspect of the invention. Percentages are by weight.

EXAMPLE 4

An emulsifiable concentrate is made up by mixing and stirring the ingredients until all are dissolved.

| | |
|---|---|
| Compound No. 3 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 5

The active ingredient is dissolved in methylene dichloride and the resultant liquid sprayed on to the granules of attapulgite clay. The solvent is then allowed to evaporate to produce a granular composition.

| | |
|---|---|
| Compound No. 3 of Table I | 5% |
| Attapulgite granules | 95% |

EXAMPLE 6

A composition suitable for use as a seed dressing is prepared by grinding and mixing the three ingredients.

| | |
|---|---|
| Compound No. 3 of Table I | 50% |
| Mineral oil | 2% |
| China clay | 48% |

EXAMPLE 7

A dustable powder is prepared by grinding and mixing the active ingredient with talc.

| | |
|---|---|
| Compound No. 3 of Table I | 5% |
| Talc | 95% |

EXAMPLE 8

A suspension concentrate is prepared by ball milling the ingredients to form an aqueous suspension of the ground mixture with water.

| | |
|---|---|
| Compound No. 3 of Table I | 40% |
| Sodium lignosulphonate | 10% |
| Bentonite clay | 1% |
| Water | 49% |

This formulation can be used as a spray by diluting into water or applied directly to seed.

EXAMPLE 9

A wettable powder formulation is made by mixing together and grinding the ingredients until all are throughly mixed.

| | |
|---|---|
| Compound No. 3 of Table I | 25% |
| Sodium lauryl sulphate | 2% |
| Sodium lignosulphonate | 5% |
| Silica | 25% |
| China clay | 43% |

EXAMPLE 10

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace —5% of disease on untreated plants
2 = 6-25% of disease on untreated plants
1 = 26-59% of disease on untreated plants
0 = 60-100% of disease on untreated plants The results are shown in Table III.

TABLE III

| Compound No | Puccinia recondita (Wheat) | Erysiphe graminis (Barley) | Venturia inaequalis (Apple) | Pyricularia oryzae (Rice) | Cercospora arachidicola (Peanut) | Plasmopara viticola (Vine) | Septoria nodorum |
|---|---|---|---|---|---|---|---|
| 1 | 4 | 4 | 4 | 0 | 0 | 0 | |
| 2 | 4 | 4 | 4 | 3 | 0 | 0 | |
| 3 | 4 | 4 | 4 | 3 | 4 | 0 | |

TABLE III-continued

| Compound No | Puccinia recondita (Wheat) | Erysiphe graminis (Barley) | Venturia inaequalis (Apple) | Pyricularia oryzae (Rice) | Cercospora arachidicola (Peanut) | Plasmopara viticola (Vine) | Septoria nodorum |
|---|---|---|---|---|---|---|---|
| 4 | 4 | 4 | 4 | 3 | 0 | 4 | |
| 5 | 4 | 4 | 4 | 0 | 1 | 0 | |
| 6 | 1 | 2 | 3 | 0 | 0 | 0 | |
| 7 | 3 | — | 0 | 0 | 3 | 0 | — |
| 8 | 4 | 4 | 4 | 3 | 4 | 0 | — |
| 16 | 0 | — | 0 | 0 | — | 0 | 1 |

What is claimed is:

1. A compound of formula (II):

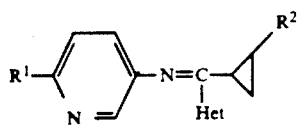

and in E- or Z-isomeric form, wherein R¹ is hydrogen, halogen, C₁₋₁₄ alkoxy, C₁₋₄ alkyl, C₂₋₄ alkenyl, C₂₋₄ alkynyl, C₁₋₄ haloalkyl, C₁₋₄ haloalkoxy, C₂₋₄ alkenyloxy, C₁₋₄ alkylcarbonyl, or cyano; R² is hydrogen, C₁₋₄ alkyl, C₁₋₄ haloalkyl or halogen; Het is a nitrogen-linked imidazole, pyrazole, 1,2,4-triazole, tetrazole or pyrrole ring which is optionally substituted by C₁₋₄ alkyl; and metal complexes and acid addition salts thereof.

2. A compound as claimed in claim 1 having the formula (II):

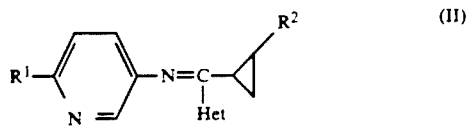

and in E- or Z-isomeric form, wherein R¹ is hydrogen, halogen, C₁₋₁₄ alkoxy; R² is hydrogen, halogen or C₁₋₄ alkyl; and Het is a nitrogen-linked imidazole, pyrazole, 1,2,4-triazole, tetrazole or pyrrole ring which is optionally substituted by C₁₋₄ alkyl.

3. A compound as claimed in claim 1 having the formula (II):

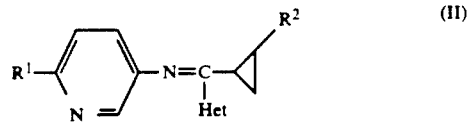

and in E- or Z-isomeric form, wherein R¹ is halogen or C₁₋₁₄ alkoxy; R² is hydrogen or halogen; and Het is a nitrogen-linked imidazole, pyrazole, 1,2,4-triazole, tetrazole or pyrrole ring.

4. A compound as claimed in claim 1 have the formula (II):

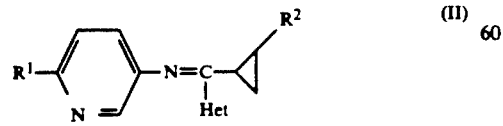

and in E- or Z-isomeric form wherein R¹ is chlorine, fluorine or methoxy; R² is hydrogen, fluorine or chlorine; and Het is a nitrogen-linked imidazole, pyrazole, 1,2,4-triazole, tetrazole or pyrrole ring containing 1, 2, or 3 nitrogen atoms and, optionally an oxygen or a sulphur atom.

5. A compound as claimed in claim 1 having the formula (II):

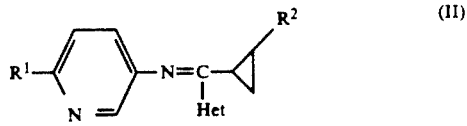

and in E- or Z-isomeric form, wherein R¹ is chlorine, fluorine or methoxy; R² is hydrogen; and Het is a nitrogen-linked imidazole, pyrazole or 1,2,4-triazole ring containing 1, 2 or 3 nitrogen atoms.

6. A compound as claimed in claim 2 having the formula II:

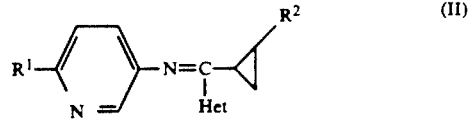

and in E- or Z-isomeric form, wherein R¹ is chlorine, fluorine or methoxy; R² is hydrogen; and Het is a nitrogen-linked imidazole, pyrazole or 1,2,4-triazole ring containing 1, 2, or 3 nitrogen atoms.

7. A compound as claimed in claim 3 having the formula II:

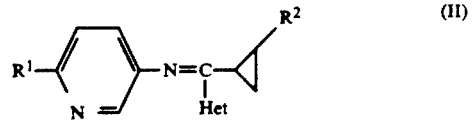

and in E- or Z-isomeric form, wherein R¹ is chlorine, fluorine or methoxy; R² is hydrogen; and Het is a nitrogen-linked imidazole, pyrazole or 1,2,4-triazole ring containing 1, 2, or 3 nitrogen atoms.

8. A compound as claimed in claim 4 having the formula II:

and in E- or Z-isomeric form, wherein R¹ is chlorine, fluorine or methoxy; R² is hydrogen; and Het is a nitrogen-linked imidazole, pyrazole or 1,2,4-triazole ring containing 1, 2 or 3 nitrogen atoms.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a compound according to claim 1.

11. A method of combating fungi which comprises applying to plants, to the seeds of plants or to the locus of the plants or seeds, a composition according to claim 9.

* * * * *